United States Patent [19]

Almeter et al.

[11] Patent Number: 5,148,217
[45] Date of Patent: Sep. 15, 1992

[54] ELECTROSTATOGRAPHIC COPIER/PRINTER DENSITOMETER INSENSITIVE TO POWER SUPPLY VARIATIONS

[75] Inventors: David D. Almeter, Rochester; William A. Resch, III, Pittsford, both of N.Y.

[73] Assignee: Eastman Kodak Company, Rochester, N.Y.

[21] Appl. No.: 719,452

[22] Filed: Jun. 24, 1991

[51] Int. Cl.⁵ .............................................. G03G 15/00
[52] U.S. Cl. .................................... 355/203; 355/246; 307/311; 328/161; 356/445
[58] Field of Search ............... 355/203, 204, 208, 246; 356/436, 445; 328/145, 161; 307/311, 490–492, 498; 118/691

[56] References Cited

U.S. PATENT DOCUMENTS

| | | |
|---|---|---|
| 3,911,861 | 10/1975 | Griesmer .............................. 118/691 |
| 3,955,096 | 5/1976 | Faulhaber ............................ 328/161 |
| 4,080,075 | 3/1978 | Berg ..................................... 328/145 |
| 4,553,033 | 11/1985 | Hubble et al. ....................... 250/353 |

FOREIGN PATENT DOCUMENTS 56-78857  6/1981  Japan .................................. 355/246

Primary Examiner—Joan H. Pendegrass
Attorney, Agent, or Firm—David A. Howley

[57] ABSTRACT

A densitometer includes a light source positioned to project light rays to a test surface. A photodetector is positioned to receive light rays from the surface, and has an output which is characteristic of the amount of light received. The densitometer includes a voltage source and a photodetector which generates an output signal which is a function of a measured density and of the voltage of the source. A log amp produces a signal which is substantially proportional to the ratio of the output of the photodetector and a second output signal which is also a function of the voltage of the source.

8 Claims, 3 Drawing Sheets

ELECTROSTATOGRAPHIC COPIER/PRINTER DENSITOMETER INSENSITIVE TO POWER SUPPLY VARIATIONS

BACKGROUND OF THE INVENTION

1. Technical Field

This invention relates generally to densitometers for measuring the relative optical density of a developed toner image on a test patch for controlling process parameters in electrostatographic apparatus such as copiers and/or printers.

2. Background Art

In electrostatographic apparatus such as printers and/or copiers, regulation of process control parameters is required to produce images having constant and predeterminable densities. Such control parameters include electrical charger energization, exposure energy, development bias voltage, toner concentration, and image transfer potential.

One method of monitoring the effect of the process control parameters is to measure the transmissive or reflective optical density of a toner image on an exposed and developed area (called a "patch") of an image receiver. Known techniques for measuring the optical density of the developed toner image include the use of infrared densitometers.

According to a typical prior art device, such densitometers generally include a light generator such as an LED., a transducer for converting the light transmitted by, or reflected from, the patch to an electrical signal current; and a sensing circuit for comparing the signal current to a reference current, and for producing a difference or ratio signal. Such densitometers suffer from a dependency on the provision of a constant current, both to the light generator and for the reference current; as fluctuations in one of these currents would affect the difference or ratio signal. Accordingly, densitometers are usually powered by at least one constant current source so that fluctuations in line voltage do not affect either the amount of current to the light source or the reference current.

In other prior systems, at least one of the constant current sources is replaced by a constant intensity illumination source. See for example U.S. Pat. No. 4,553,033, which issued to Hubble et al. on Nov. 12, 1985.

DISCLOSURE OF INVENTION

It is an object of the present invention to provide a densitometer which does not require the use of either constant current sources in the power supply circuit or constant illumination sources.

It is another object of the present invention to provide a densitometer which is powered by a single voltage source in a circuit that does not require the use of either constant current source or constant illumination sources.

According to one aspect of the present invention, a densitometer includes a light source positioned to project light rays to a test surface. A photodetector is positioned to receive light rays from the surface, and has an output which is characteristic of the amount of light received. According to a preferred feature of the present invention, a densitometer includes a voltage source and a photodetector which generates an output signal which is a function of a measured density and of the voltage of the source, A log amp produces a signal which is substantially proportional to the ratio of the output of the photodetector and a second output signal which is also a function of the voltage of the source.

The invention, and its objects and advantages, will become more apparent in the detailed description of the preferred embodiments presented below.

BRIEF DESCRIPTION OF THE DRAWINGS

In the detailed description of the preferred embodiments of the invention presented below, reference is made to the accompanying drawings, in which.

BEST MODE FOR CARRYING OUT THE INVENTION

Figure 1:
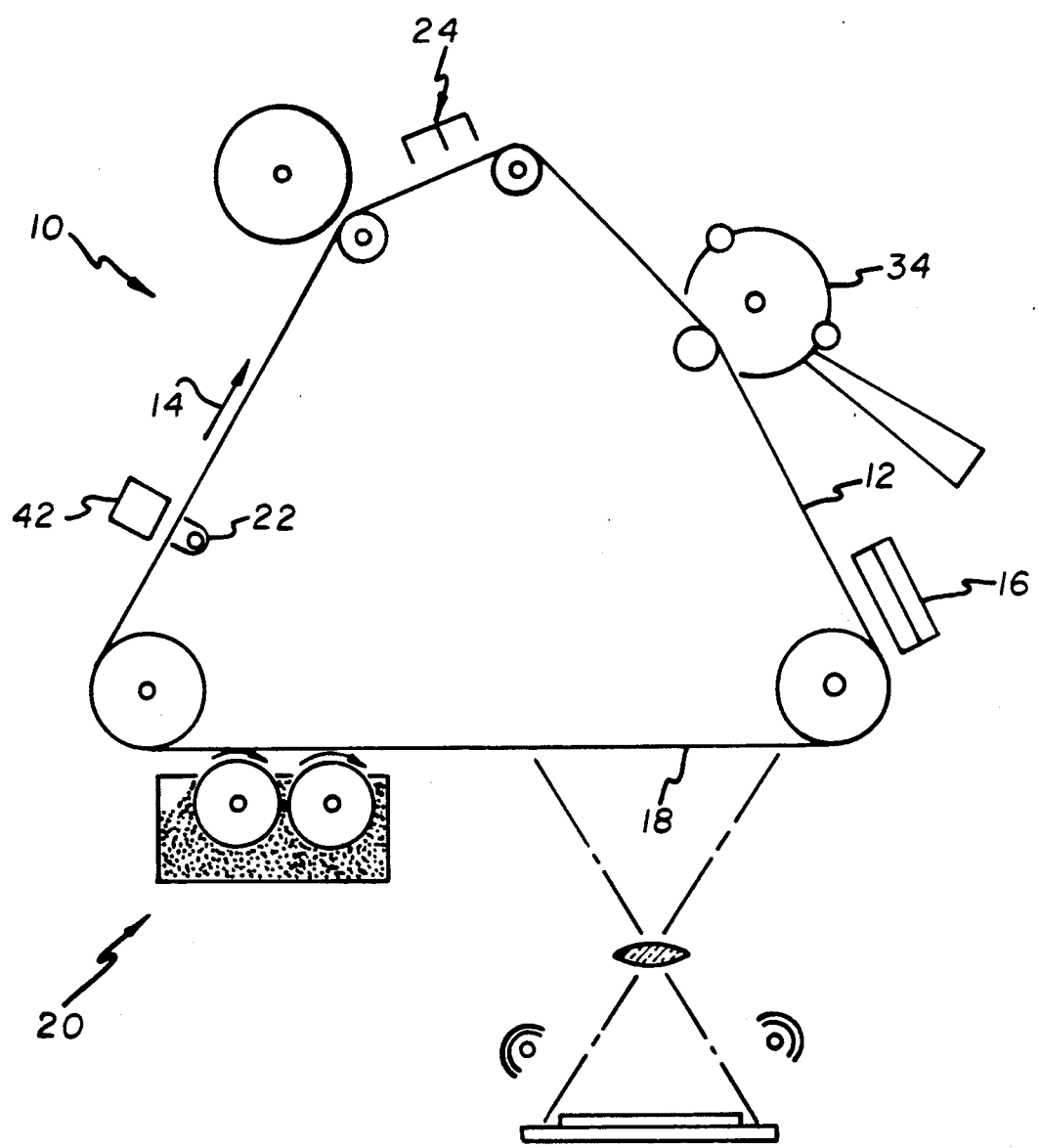
FIG. 1 is a vertical schematic representation of an electrostatographic machine with which the present invention is usable.

FIG. 1 shows an electrophotographic machine 10 having an image receiver in the form of a photoconductive belt 12 which moves in a clockwise direction, as represented by an arrow 14.

An electrostatic charge is applied to belt 12 at a charging station 16. Images are projected onto belt 12 at an exposure station 18, providing a suitable interframe distance between image areas. The projected light images dissipate the electrostatic charge at the exposed areas of the photoconductive belt to form a latent electrostatic image on belt 12.

The latent electrostatic image on belt 12 is developed with toner at a developer station 20. The toner image is then subjected to radiation by a post-development erase lamp 22 to reduce the electrical stress on photoconductive belt 12 and to reduce the attraction between the toner image and belt 12.

As the toner image on belt 12 approaches a transfer station 24, a copy sheet is fed from a supply (not shown). Transfer station 24 serves as a means to effect the movement of the toner image to copy sheet (not shown) by applying a charge opposite in polarity to that of the toner image and neutralizing the charge on the copy sheet so that it easily separates from belt 12. The copy sheet bearing toner is then passed through a pair of heated fuser rollers (not shown). Mechanical and electrical cleaning of photoconductive belt 12 is effected at a cleaning station 34.

Figure 2:
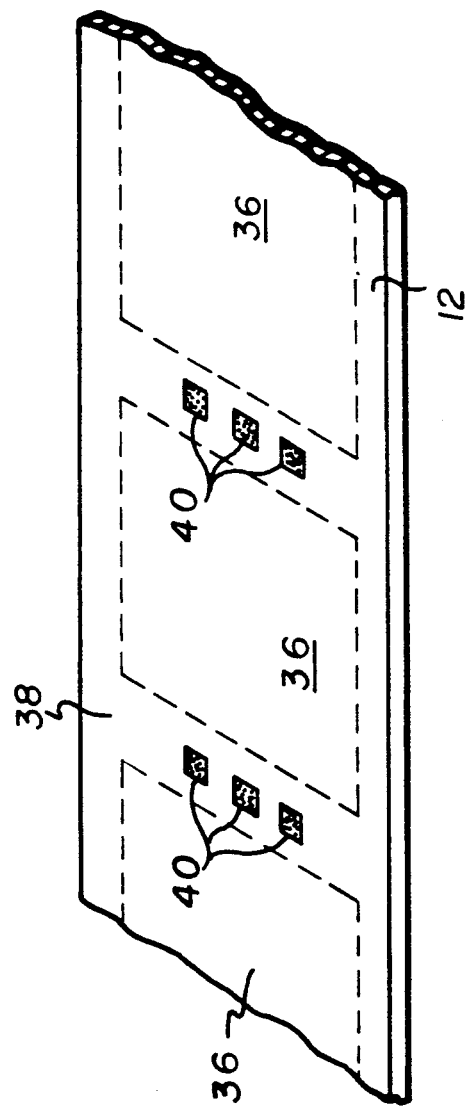
FIG. 2 is an enlarged fragmentary perspective view of a portion of the electrostatographic machine of FIG. 1.

Referring to FIG. 2, photoconductive belt 12 is illustrated with a plurality of image areas of film frames 36 spaced slightly apart from each other along the longitudinal length of the belt; thus defining non-image interframe regions 38.

In order to control the electrographic process, it is known to provide one or more test patches 40 of toner in interframe regions 38. The test patches can be formed by leaving such areas charged when the other parts of the photoconductive belt outside image areas 36 are discharged, and then exposing the area to a predetermined level of irradiation. Then toner is applied to the test patches by development station 20 of FIG. 1. In this manner the density of toner on the test patches is directly related to the density of toner in image areas 36. By way of example, three toned test patches 40 are shown adjacent to each other in each interframe region 38. However, more or fewer test patches could be provided if desired. When multiple test patches for each interframe region are used for density measurement, the patches preferably are exposed to obtain different density levels of toner so that the electrographic process can be checked and controlled for various operating parameters.

Referring back to FIG. 1, as test patches 40 pass a transmission densitometer 42, light rays from erase lamp 22 or other light source pass through belt 12 and each test patch to an associated photodetector. A reflection densitometer may be used. A signal generated by densitometer 42 is provided to a logic and control unit (not shown) which is programmed to provide various control signals to portions of the apparatus in response to the signal received from the densitometer. For example, the control signal from the densitometer can cause the logic and control unit to regulate a number of process parameters such as the voltage applied to photoconductive belt 12 at charging station 16, the intensity or duration of exposure at station 18, the bias voltage of development station 20, and/or the concentration of toner in the developer mixture. In general, the signal from densitometer 42 can be used to control any process parameter that effects the density of the toner images on the photoconductor.

Figure 3:
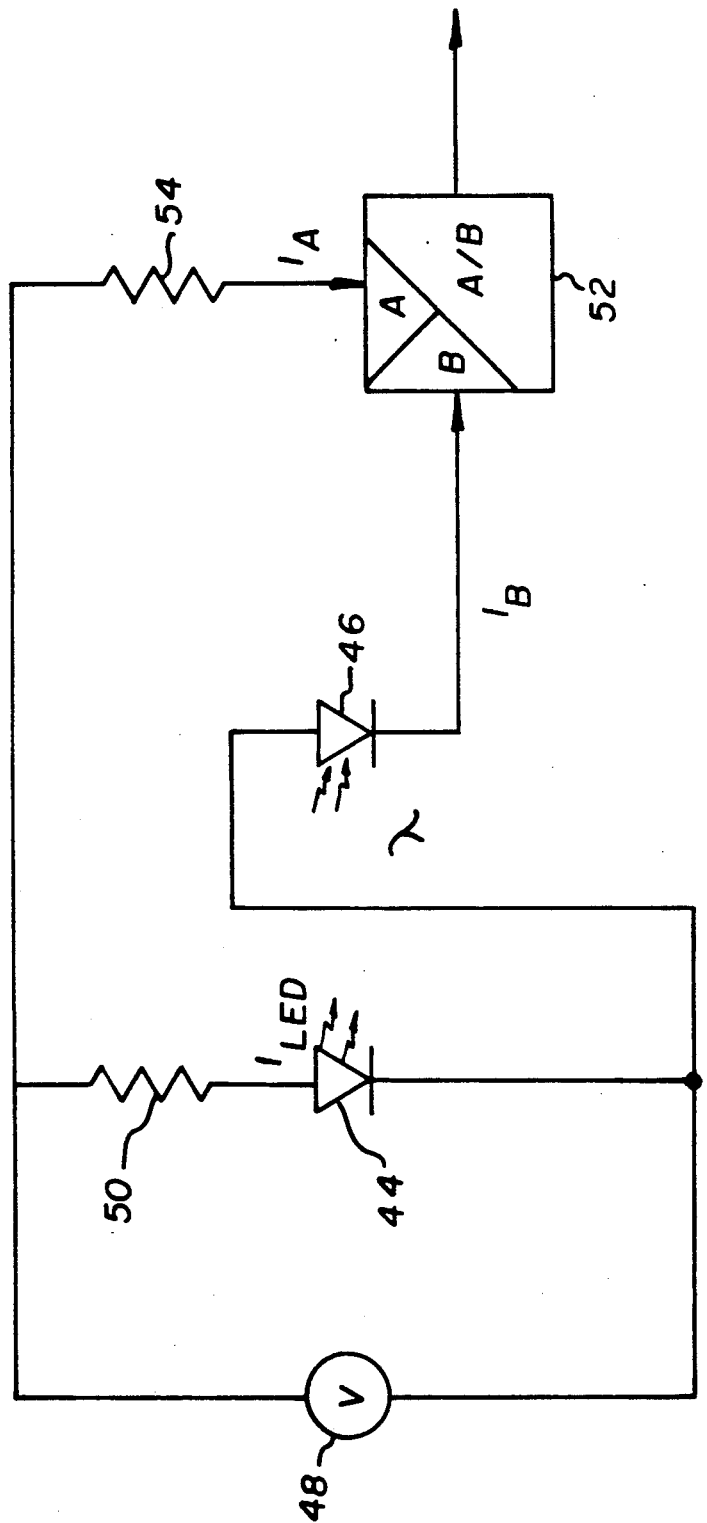
FIG. 3 is a schematic of a densitometer circuit of the machine of FIGS. 1 and 2.

FIG. 3 is a schematic of the circuit of densitometer 42 of FIG. 1. A light emitting diode 44 is aligned with a photodetector 46 such that the photodiode collects at least a portion of the radiation from the light emitting diode which is transmitted through or reflected from photoconductive belt 12 of FIG. 1. The signal $I_b$ from photodetector 46 includes an output current component which is characteristic of the amount of reflected light received, which is in turn directly related to the current $I_{LED}$ to LED 44. Of course, current $I_{LED}$ is itself a function of voltage source 48 and a resistor 50.

Signal $1_B$ is inputted to a ratio-to-signal converter 52, which produces an output signal related to the ratio of a current $I_A$ and signal $I_B$. Current $I_A$ is a function of voltage source 48 and a resistor 54.

It is now apparent that the output signal from ratio-to-signal converter 52 is directly related to $I_A$ and inversely related to $I_{LED}$. Since both $I_A$ and $I_{LED}$ are directly related to the output of voltage source 48, errors in the output of ratio-to-signal converter 52 caused by fluctuations in the voltage output of source 48 tend to cancel so that the output signal is therefore directly related to the ouput of voltage source.

Ratio-to-signal converter 52 may take various forms, well known in the art. For example, the converter may be a logarithmic amplifier which produces an output signal which is related to the log of the ratio of $I_A$ and $1_B$. Such a logarithmic amplifier is manufactured by Intersil as the ICL8048.

The invention has been described in detail with particular reference to preferred embodiments thereof, but it will be understood that variations and modifications can be effected within the spirit and scope of the invention.

What is claimed is:

1. A densitometer comprising:
   a voltage source;
   first means powered by said voltage source for generating an output signal which is a function of a measured density and of the voltage of said source;
   second means for directly monitoring the voltage of said source to generate an output signal which is a function of the voltage of said source; and
   third means powered by said source for producing a signal which is substantially proportional to the ratio of the outputs of the first and second means.

2. A densitometer as defined in claim 1 wherein the output signals of said first and second means are substantially linear functions of the voltage of said source.

3. A densitometer as defined in claim 1 wherein the signal produced by said third means is substantially proportional to the ratio of the simultaneous outputs of the first and second means.

4. A densitometer as defined in claim 1 wherein said output signals generated by said first and second means are currents.

5. A densitometer as defined in claim 4 wherein said first and second means comprise resistors.

6. A densitometer as defined in claim 1 wherein said first means comprises a photodetector and a radiation source powered by said voltage source.

7. A densitometer as defined in claim 1 wherein said third means comprises a logarithmic amplifier.

8. An electrostatographic copier/printer having process control parameters determined in accordance with the optical density of a toned test patch as measured by a densitometer comprising:
   a voltage source;
   first means powered by said voltage source for generating an output signal which is a function of a measured density and of the voltage of said source;
   second means for directly monitoring the voltage of said source to generate an output signal which is a function of the voltage of said source; and
   third means powered by said source for producing a signal which is substantially proportional to the ratio of the outputs of the first and second means.

* * * * *